US011826201B2

United States Patent
Errico et al.

(10) Patent No.: US 11,826,201 B2
(45) Date of Patent: Nov. 28, 2023

(54) ULTRASOUND LESION ASSESSMENT AND ASSOCIATED DEVICES, SYSTEMS, AND METHODS

(71) Applicant: KONINKLIJKE PHILIPS N.V., Eindhoven (NL)

(72) Inventors: Claudia Errico, Cambridge, MA (US); Christine Menking Swisher, San Diego, CA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 517 days.

(21) Appl. No.: 17/251,804

(22) PCT Filed: Jun. 18, 2019

(86) PCT No.: PCT/EP2019/066044
§ 371 (c)(1),
(2) Date: Dec. 13, 2020

(87) PCT Pub. No.: WO2019/243344
PCT Pub. Date: Dec. 26, 2019

(65) Prior Publication Data
US 2021/0113190 A1    Apr. 22, 2021

Related U.S. Application Data

(60) Provisional application No. 62/688,505, filed on Jun. 22, 2018.

(51) Int. Cl.
*G06K 9/00* (2022.01)
*A61B 8/08* (2006.01)
(Continued)

(52) U.S. Cl.
CPC .............. *A61B 8/481* (2013.01); *A61B 8/461* (2013.01); *A61B 8/469* (2013.01); *G06N 3/047* (2023.01);
(Continued)

(58) Field of Classification Search
CPC ......... A61B 8/481; A61B 8/461; A61B 8/469; A61B 8/06; A61B 8/4472; A61B 8/463;
(Continued)

(56) References Cited

U.S. PATENT DOCUMENTS 5,776,063 A * 7/1998 Dittrich ................. A61B 8/481
600/458
2011/0176710 A1* 7/2011 Mattiuzzi .............. G06T 7/0012
382/128
(Continued)

FOREIGN PATENT DOCUMENTS

RO    128001 B1    2/2016

OTHER PUBLICATIONS

Barber: "The Use of Principal Components in the Quantitative Analysis of Gamma Camera Dynamic Studies": Physics in Medicine & Biology, vol. 25, pp. 283-292.
(Continued)

*Primary Examiner* — Shervin K Nakhjavan (57) ABSTRACT

Clinical assessment devices, systems, and methods are provided. A clinical assessment system, comprising a processor in communication with an imaging device, wherein the processor is configured to receive, from the imaging device, a sequence of image frames representative of a contrast agent perfused subjects tissue across a time period; classify the sequence of image frames into a plurality of first tissue classes and a plurality of second tissue classes based on a spatiotemporal correlation among the sequence of image frames by applying a predictive network to the sequence of
(Continued)

image frames to produce a probability distribution for the plurality of first tissue classes and the plurality of second tissue classes; and output, to a display in communication with the processor, the probability distribution for the plurality of first tissue classes and the plurality of second tissue classes.

18 Claims, 9 Drawing Sheets

(51) Int. Cl.
 A61B 8/00 (2006.01)
 G06T 7/00 (2017.01)
 G06N 3/047 (2023.01)

(52) U.S. Cl.
 CPC .. *G06T 7/0012* (2013.01); *G06T 2207/10016* (2013.01); *G06T 2207/10132* (2013.01); *G06T 2207/20081* (2013.01); *G06T 2207/20084* (2013.01); *G06T 2207/30056* (2013.01); *G06T 2207/30096* (2013.01); *G06T 2207/30104* (2013.01)

(58) Field of Classification Search
 CPC .... A61B 8/5276; A61B 8/5223; G06N 3/047; G06N 3/044; G06N 3/045; G06N 3/048; G06N 3/084; G06T 7/0012; G06T 2207/10016; G06T 2207/10132; G06T 2207/20081; G06T 2207/20084; G06T 2207/30056; G06T 2207/30096; G06T 2207/30104; G06T 7/0016; G16H 30/40; G16H 50/20; G16H 50/30
 See application file for complete search history.

(56) References Cited

U.S. PATENT DOCUMENTS

| | | | |
|---|---|---|---|
| 2015/0297172 A1 | 10/2015 | Takagi et al. | |
| 2018/0276821 A1* | 9/2018 | Lin | A61B 8/5223 |
| 2018/0330818 A1* | 11/2018 | Hsieh | G16H 40/60 |
| 2019/0236782 A1* | 8/2019 | Amit | G06T 7/0016 |
| 2020/0226748 A1* | 7/2020 | Kaufman | G06F 18/254 |
| 2023/0160987 A1* | 5/2023 | Wang | A61B 5/7203 |
| | | | 382/128 |

OTHER PUBLICATIONS

Botoca et al: "Cellular Neural Network Processing of CEUS Examination. A Pilot Study"; 2016 IEEE, 4 Page Document.
Brannigan et al: "Blood Flow Patterns in Focal Liver Lesions at Microbubble-Enhanced US"; Radiographics, 2004, pp. 921-935.
Chiorean et al: "Vascular Phases in Imaging and Their Role Fin Focal Liver Lesions6\Assessment"; Clinical Hemorheology and Microcirculation, vol. 62, No. 4, pp. 299-326, 2016.
Chung et al: "Contrast-Enhanced Ultrasonography:Advance and Current Status in Abdominal Imaging"; Ultrasonography, 2015, vol. 34, pp. 3-18.
Claudon et al: "Guidelines and Good Clinical Practice Recommendations for Contrast Enhanced Ultrasound (CEUS) in the Liver—Update 2012"; Ultraschall in Med, vol. 34, pp. 11-29.
Dietrich et al: "Contrast Enhanced Ultrasound:Liver Imaging Reporting and Data System (CEUS LI-RADS)"; Ultrasound in Medicine and Biology, vol. 43, T4-14-IN10, pp. S38-S39, 2017.
Esteva et al: "Dermatologist-Level Classification of Skin Cancer With Deep Nerual Networks"; Nature 21056, Feb. 2017, vol. 542, 12 Page Article.
Forner et al: "Hepatocellular Carcinoma"; Lancet 2018, 391, pp. 1301-1314.
Jang et al: "Contrast-Enhanced Ultrasound in the Detection and Characterization of Liver Tumors"; Cancer Imaging (2009), vol. 9, pp. 96-103.
CEUS LI-RADS v2017 Core (For CEUS With Pure Blood Pool Agents); 2017, 27 Page Document.
Liang et al: "Recognizing Focal Liver Lesions in CEUS With Dynamically Trained Latent Structured Models"; IEEE Transactions on Medical Imaging, vol. 35, No. 3, Mar. 2016, pp. 713-.
Center for Disease Control and Prevention: "Liver Cancer"; 2017, Downloaded from https//www.cdc.gov/cancer/liver/indezx.htm, 4 page document.
PCT/EP2019/066044 ISR & WO, Oct. 22, 2019, 16 Page Document.
Piscaglia et al: "Contrast Enhanced Ultrasound Liver Imaging Reporting and Data System (CEUS LI-RADS) for the Diagnosis of Hepatocellular Carcinoma:A Pictorial Essay"; American College of Radiology, 2017;38, pp. 320-324.
Quatrehomme et al: "Assessing the Classification of Liver Focal Lesions by Using Multi-Phase Computer Tomography Scans"; MC BR-CDS 2012, LNCS 7723, pp. 80-91, 2013.
Shiraishi et al: "Computer-Aided Diagnosis for Classification of Focal Liver Lesions on Contrast-Enhanced Ultrasonography: Feature Extraction and Characterization of Vascularity Patterns"; Medical Imaging 2008, Proc. of SPIE, vol. 6915, pp. 691532-1-691532-11.
Streba et al: "Contrast-Enhanced Ultrasonography Parameters in Neural Network Diagnosis of Liver Tumors"; World J Gastroenterol 2012, 18(32), pp. 4427-4434.
Ta et al: "Automating Tumor Classification With Pixel-By-Pixel Contrast-Enhanced Ultrasound Perfusion Kinetics"; American Vacuum Society, 2012, 02C103-1-02.
Wilson et al: "An Algorithm for the Diagnosis of Focal Liver Masses Using Microbubble Contrast-Enhanced Pulse-Inversion Sonography"; Hepatobiliary Imaging, May 2006, pp. 1401-1412.
Wu et al: "Deep Learning Based Classification of Focal Liver Lesions With Contrast-Enhanced Ultrasound": Optik 125 (2014), pp. 4057-4063.

* cited by examiner

ULTRASOUND LESION ASSESSMENT AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2019/066044, filed on Jun. 18, 2019, which claims the benefit of U.S. Provisional Patent Application No. 62/688,505, filed on Jun. 22, 2018. These applications are hereby incorporated by reference herein.

TECHNICAL FIELD

The present disclosure relates generally to ultrasound imaging and, in particular, to providing automated systems and methods for assessing lesions.

BACKGROUND

Medical ultrasound imaging is a medical imaging modality that is often preferred over contrast-enhanced computed tomography (CT), or magnetic resonance imaging (MRI), for its accessibility, inexpensiveness, safety, and simplicity to use, and more importantly for its real-time feedback. For example, B-mode imaging, color Doppler imaging, and/or power Doppler imaging are commonly used to characterize soft tissues, retrieve vasculature information, and quantify blood flow. However, in some specific applications, such as focal liver lesion (FLL) characterization and classification, the fore mentioned ultrasound imaging modalities may lack of specificity and sensitivity. In such a case, contrast-enhanced ultrasound (CEUS) imaging may be a preferred ultrasound imaging mode as it provides morphological and vascular enhancement information.

In CEUS imaging, stabilized gas-filled microbubbles are used as contrast agents to increase the detectability of blood flow under ultrasound imaging. For example, a patient may be injected with a bolus of microbubbles via an antecubital vein. The microbubbles may flow through the patient's body including the hepatic artery and the portal vein, which supply blood to the liver. The dynamics (e.g., the fill-in and the wash-out) of the microbubbles in the hepatic artery and the portal vein can be used to differentiate whether a lesion is benign (i.e. solid or cystic masses) or malignant (i.e. hyper-vascular lesions). In addition, FLLs of different natures may have different vascular enhancement patterns under imaging. The spatiotemporal properties of the vascular enhancement patterns in combination with the microbubble dynamics can be used to classify and characterize the nature of liver lesions. However, the analysis, classification, and characterization may be complex and the differences among different types or different classes of liver lesions can be subtle, and thus may require expert knowledge.

SUMMARY

While existing ultrasound imaging has proved useful for clinical assessments and diagnosis, there remains a clinical need for improved systems and techniques for providing automated lesion assessment tools. Embodiments of the present disclosure provide a deep learning framework to assist and guide a user in classification and characterization of a lesion (e.g., a hepatic lesion) via CEUS imaging. The disclosed embodiments may apply a three-dimensional (3D) deep learning predictive network to a sequence of CEUS images capture from a patient across a period of time after injecting the patient with contrast agents (e.g., microbubbles). The deep learning predictive network may classify the sequence of image frames into malignant versus benign, and further into subclasses of malignant or benign lesions. The deep learning predictive network may be trained to learn spatiotemporal characteristics of microbubble dynamics (filling-in/wash-out) and/or blood-flow enhancement patterns (e.g., during an arterial phase, a portal venous phase, and/or a late phase) in a lesion for different lesion types and/or states. In addition, the disclosed embodiments may extract high-level diagnostic information from the deep learning predictive network and may present the interpretations of the CEUS image in the form of a text report. Further, the disclosed embodiment may identify image frames (e.g., decisive frames) from the sequence that include the most significant features (e.g., spatiotemporal signatures) contributing to the classification output. The classification, the text report, and/or the decisive frames can guide a user in lesion assessment.

In one embodiment, a clinical lesion assessment system includes a processor in communication with an imaging device, wherein the processor is configured to receive, from the imaging device, a sequence of image frames representative of a subject's tissue perfused with a contrast agent across a time period; classify the sequence of image frames into a plurality of first tissue classes and a plurality of second tissue classes different from the first tissue classes, the classification based on a spatiotemporal correlation among the sequence of image frames by applying a predictive network to the sequence of image frames to produce a probability distribution for the plurality of first tissue classes and the plurality of second tissue classes; and output, to a display in communication with the processor, the probability distribution for the plurality of first tissue classes and the plurality of second tissue classes.

In some embodiments, the processor is further configured to output, to the display, a probability for each of the plurality of first tissue classes; and output, to the display, a probability for each of the plurality of second tissue classes. In some embodiments, the predictive network identifies a subset of the sequence of image frames that are most representative of the probability distribution, and wherein the processor is further configured to output, to the display, an image frame in the subset. In some embodiments, the spatiotemporal correlation is among pixels in the sequence of image frames representing perfusion of the contrast agent through the subject's tissue. In some embodiments, the predictive network produces a text report including information associated with the perfusion of the contrast agent through the subject's tissue during different sub-periods within the time period based on the spatiotemporal correlation, and wherein the processor is further configured to output, to the display, the text report. In some embodiments, the predictive network includes a first predictive sub-network and a second predictive sub-network, wherein the first predictive sub-network produces the probability distribution, and wherein the second predictive sub-network produces the text report. In some embodiments, the sub-periods include at least one of an arterial phase (AP) of the perfusion, a portal venous phase (PVP) of the perfusion, or a late phase of the perfusion. In some embodiments, the subject's tissue includes at least a portion of a liver. In some embodiments, the plurality of first tissue classes includes at least one of hepatocellular carcinomas (HCC), cholangiocarcinoma, or metastasis, and wherein the plurality of second tissue classes includes at least one of hemangioma, focal nodular hyperplasia (FNH), or adenoma. In some embodiments, the processor is configured to output, to the display, a brightness-mode (B-mode) image representative of the subject's tissue. In some embodiments, the processor is configured to output, to the display, a contrast-enhanced image of the subject's tissue based on the sequence of image frames. In some embodiments, the processor is further configured to receive, from a user input device in communication with the processor, an indication of a selected region of interest (ROI) of the subject's tissue; and apply the predictive network to the sequence of image frames based on the selected ROI. In some embodiments, the processor is configured to identify a region of interest (ROI) from the subject's tissue based on the sequence of image frames; and apply the predictive network to the sequence of image frames based on the identified ROI. In some embodiments, the predictive network is trained by providing a sequence of test image frames representative of a contrast agent perfused test subject's tissue across a time period; sorting the sequence of test image frames based on an arterial phase (AP) of perfusion of the contrast agent through the test subject's tissue, a portal venous phase (PVP) of the perfusion, and a late phase of the perfusion; and assigning scores to the sequence of test image frames based on spatiotemporal characteristics of blood flow associated with the plurality of first tissue classes and the plurality of second tissue classes.

In one embodiment, a method of clinical lesion assessment includes receiving, from an imaging device, a sequence of image frames representative of a subject's tissue perfused with a contrast agent across a time period; classifying the sequence of image frames into a plurality of first tissue classes and a plurality of second tissue classes different from the first tissue classes, the classification based on a spatiotemporal correlation among the sequence of image frames by applying a predictive network to the sequence of image frames to produce a probability distribution for the plurality of first tissue classes and the plurality of second tissue classes; and displaying, by a display, the probability distribution for the plurality of first tissue classes and the plurality of second tissue classes.

In some embodiments, the displaying includes displaying a probability for each of the plurality of first tissue classes; and displaying a probability for each of the plurality of second tissue classes. In some embodiments, the method further comprises identifying, by the predictive network, a subset of the sequence of image frames that are most representative of the probability distribution; and displaying, by the display, an image frame in the subset. In some embodiments, the method further comprises generating, by the predictive network, a text report including information associated with perfusion of the contrast agent through the subject's tissue during different sub-periods of the time period based on the spatiotemporal correlation; and displaying, by the display, the text report. In some embodiments, the method further comprises identifying a region of interest (ROI) from the subject's tissue based on the sequence of image frames; and applying the predictive network based on the identified ROI. In some embodiments, the subject's tissue includes at least a portion of a liver, wherein the plurality of first tissue classes includes at least one of hepatocellular carcinoma (HCC), cholangiocarcinoma, or metastasis, and wherein the plurality of second tissue classes includes at least one of hemangioma, focal nodular hyperplasia (FNH), or adenoma.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
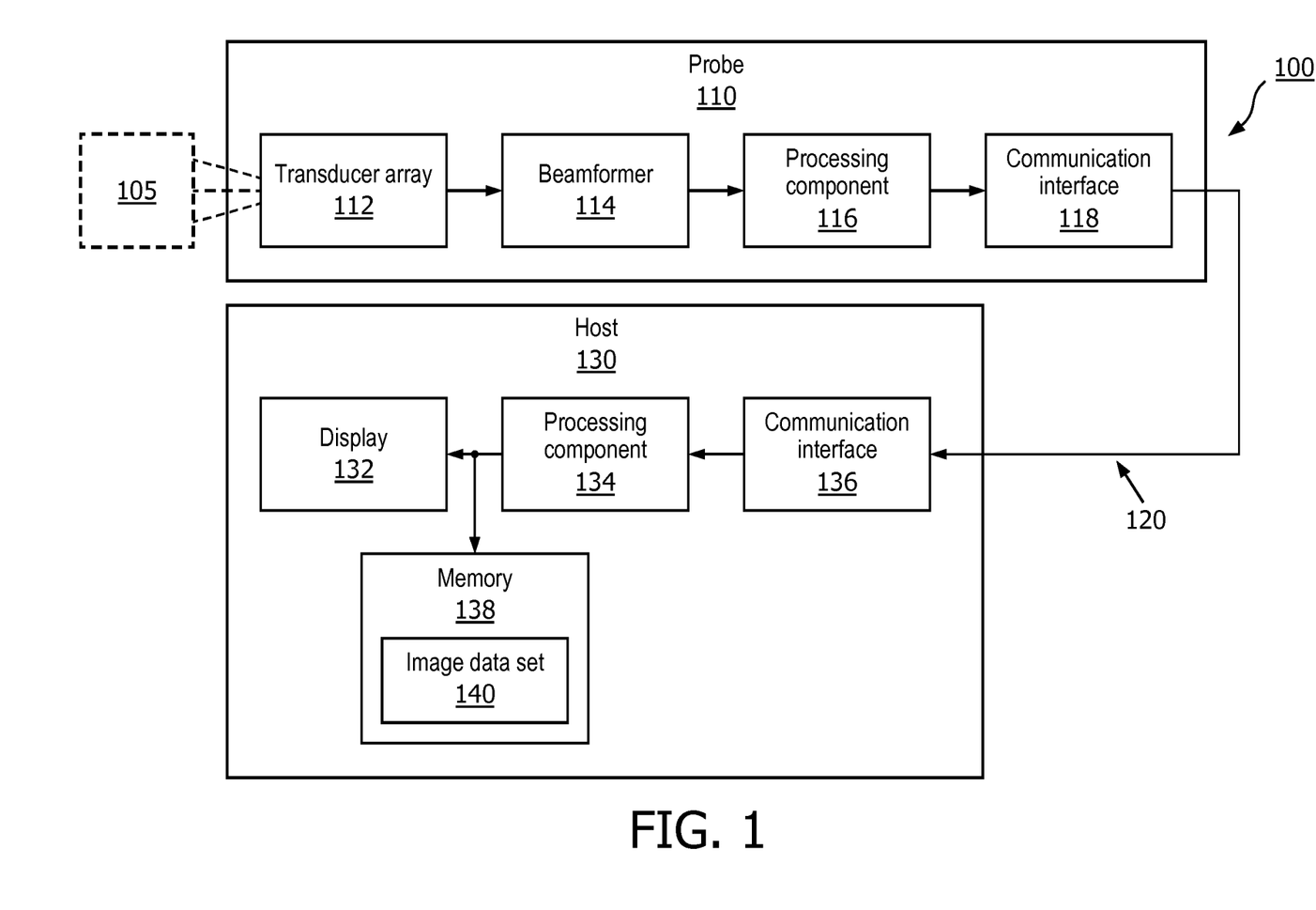
FIG. 1 is a schematic diagram of an ultrasound imaging system, according to aspects of the present disclosure.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, and a communication interface 118. The host 130 includes a display 132, a processing component 134, and a communication interface 136.

The transducer array 112 emits ultrasound signals towards an anatomical object 105 and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component.

In some embodiments, the object 105 may include at least a portion of a patient's liver for liver lesion assessment. In other embodiments, the object 105 may include any anatomy (e.g., lung, blood vessel, heart, kidney, and/or liver) of a patient that is suitable ultrasound imaging examination.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed image signals. For example, the processing component 116 may perform filtering and/or quadrature demodulation to condition the image signals. The processing component 116 and/or 134 can be configured to control the array 112 to obtain ultrasound data associated with the object 105.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processing component 134 is coupled to the communication interface 136. The processing component 134 may be implemented as a combination of software components and hardware components. The processing component 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105.

In some embodiments, the processing component 134 can perform image analysis on the image data or image frames for lesion assessments, such as focal liver lesion (FLL) assessments. The processing component 134 can apply deep-learning-based techniques to determine whether a lesion is malignant or benign and/or the type of malignant/benign lesions based on the image data or image frames, as described in greater detail herein.

The display 132 is coupled to the processing component 134. The display 132 may be a monitor or any suitable display. The display 132 is configured to display ultrasound images, image videos, and/or lesion assessment results processed by the processing component 134, as described in greater detail herein.

The system 100 can be configured for use in various stages of CEUS imaging-based lesion assessments. In an embodiment, the system 100 may be used for collecting ultrasound images to form training data set for deep learning network training. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store a CEUS image data set 140 for deep learning-based training.

In some embodiments, the system 100 may be used for training deep learning networks for lesion assessments. For example, for FLL assessment, a deep learning network may be trained using a sequence of two-dimensional (2D) contrast-enhanced image frames. The deep learning network may be trained to analyze spatiotemporal correlation among neighboring contrast-enhanced pixels (e.g., corresponding to the microbubbles) in the contrast-enhanced frames. The deep learning network may be trained to classify images into malignant and benign classes and further into malignant sub-classes and benign sub-classes.

In some embodiments, the system 100 may be used in a clinical setting for live CEUS imaging examinations, where the trained deep learning networks may be applied for lesion characterization and classification. Mechanisms for automatically and systematically assessing lesions from CEUS images based on deep learning-based techniques are described in greater detail herein.

While the system 100 is described in the context of ultrasound imaging using an ultrasound imaging probe 110, in some embodiments, the system 100 may be alternatively configured to include an imaging device for performing CT, MRI, or X-ray. In such embodiments, the processing component 134 may generate CT images, MRI images, or X-ray images for display on the display 132.

Figure 2A:
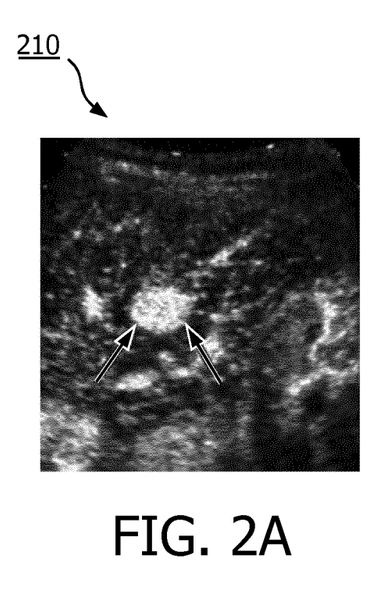
FIG. 2A is an ultrasound image of a patient's liver lesion captured from contrast-enhanced ultrasound (CEUS) imaging, according to aspects of the present disclosure.
Figure 2B:
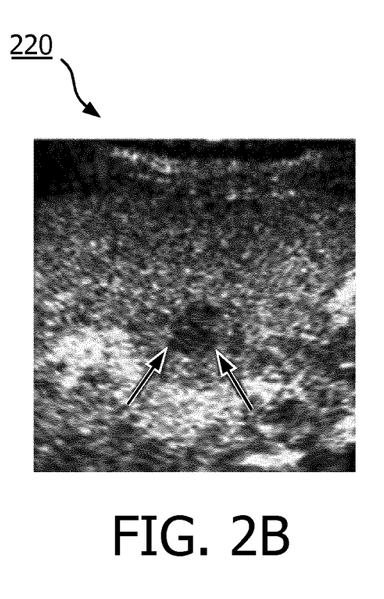
FIG. 2B is an ultrasound image of a patient's liver lesion captured from CEUS imaging, according to aspects of the present disclosure.
Figure 3A:
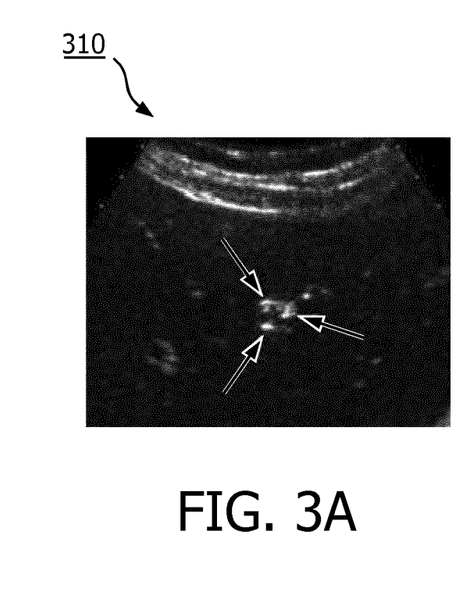
FIG. 3A is an ultrasound image of a patient's liver lesion captured from CEUS imaging, according to aspects of the present disclosure.
Figure 3B:
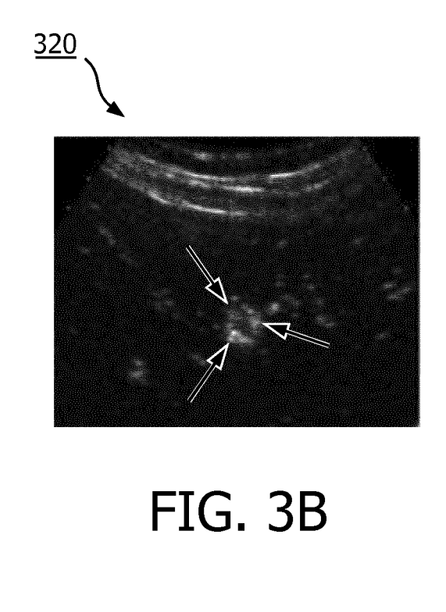
FIG. 3B is an ultrasound image of a patient's liver lesion captured from CEUS imaging, according to aspects of the present disclosure.
Figure 3C:
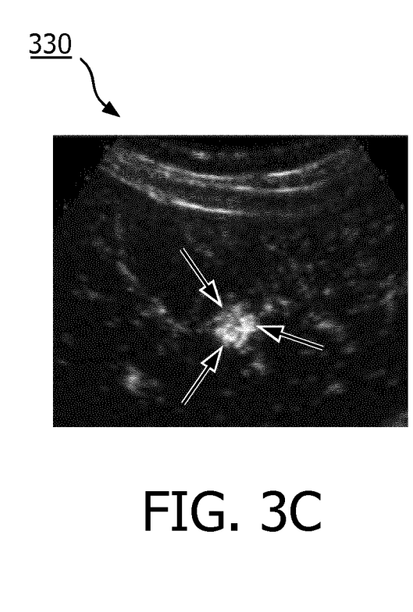
FIG. 3C is an ultrasound image of a patient's liver lesion captured from CEUS imaging, according to aspects of the present disclosure.

FIGS. 2A-2B illustrate microbubble dynamics for a malignant liver lesion at two different time instances after the administration of microbubbles. FIGS. 3A-3C illustrate microbubble dynamics for a benign liver lesion. To perform FLL assessment using CEUS imaging, a clinician may inject a bolus of microbubbles into a patient's body. The microbubbles are intravascular micron-sized phospholipid spheres. The amount of bolus injection may vary depending on the contrast agent in use. In some embodiments, the bolus injection may be between about 1 milliliter (ml) to about 5 ml. The microbubbles can enhance the detectability of the blood flow under ultrasound imaging. When microbubbles are insonified by an acoustics wave, they generate high backscattered echoes due to the high impedance mismatch between the propagating wave and their gaseous content. When the microbubbles are imaged at low mechanic index, they allow continuous imaging of both the hepatic lesion and the lesion vasculature.

The perfusion of the microbubbles through the hepatic artery and the portal vein may include an arterial phase (AP), a portal venous phase (PVP), and a late phase. The AP may begin at about 10 seconds to about 20 seconds after the injection and may last up to about 40 seconds. The PVP starts at about 40 seconds and may last up to about 2 minutes after the injection. The late phase may last up to about 4 minutes to about 6 minutes after the injection depending on the type of microbubbles used for the injection. As the dynamics of microbubble-enhanced vasculature differ for each case, the differentiation of benign versus malignant lesions may be based on the filling/washout timing versus hyper/hypo enhancement.

FIG. 2A is an ultrasound image 210 of a patient's liver lesion captured from CEUS imaging, according to aspects of the present disclosure. FIG. 2B is an ultrasound image 220 of the patient's liver lesion captured from the CEUS imaging, according to aspects of the present disclosure. The images 210 and 220 may be captured using a system similar to the system 100. The image 210 may be captured at about 24 seconds after the patient is injected with a bolus of microbubbles. The image 220 may be captured at about 169 seconds after the microbubble injection. The late-washout of the microbubbles as observed from FIGS. 2A-2B may be indicative of a malignant tumor.

FIG. 3A is an ultrasound image 310 of a patient's liver lesion captured from CEUS imaging, according to aspects of the present disclosure. FIG. 3B is an ultrasound image 320 of the patient's liver lesion captured from the CEUS imaging, according to aspects of the present disclosure. FIG. 3C is an ultrasound image 330 of the patient's liver lesion captured from the CEUS imaging, according to aspects of the present disclosure. The images 310, 320, and 330 may be captured using a system similar to the system 100. The image 310 may be captured at about 6 seconds after the patient is injected with a bolus of microbubbles. The image 320 may be captured at about 7 seconds after the microbubble injection. The image 330 may be captured at about 8 seconds after the microbubble injection. The persistent echogenicity as observed from FIGS. 3A-3C may be indicative of a benign tumor.

CEUS enables liver lesion characterization by visualizing lesion vascular morphologic characteristics and specific temporal enhancement features. In general, the AP may include information regarding the degree of vascularization within a lesion, the PVP and the late phase may provide information for defining the dynamic of the washout within the lesion with respect to surrounding tissue. Washout is defined as the transition of hyperenhancement or isoenhancement to hypoenhancement as compared to the adjacent liver parenchyma. The enhancement in the late phase may further assist in classifying malignant versus benign masses.

Benign FLLs can be classified into Hemangioma, Focal Nodular Hyperplasia (FNH), or Hepatocellular adenoma, where each may include different characteristics. For instance, haemangioma may show a globular enhancement in the peripheral area during the AP and a centripetal fill-in during the PVP, while FHN may show a spoke-wheel shaped enhancement during the AP and a hyper-enhanced central scar in the PVP and the late phase. Adenomas may present a diffuse enhancement during the AP and may become hyperechoic in the early PVP.

Malignant FLLs can be classified into hepatocellular carcinoma (HCC), intrahepatic cholangiocarcinoma (ICC), and metastasis. In some instances, malignant FLL classifications can be based on B-mode and Doppler flow images for their infiltrating vessels or hypoechoic halos. HCC may be characterized by a peripherally diffused hyper-enhancement during the AP and a delayed hypo-enhanced washout during the PVP. In some cases, when the tissue is necrotic, the affected area may show an absent enhancement. HCC washout timing may be the key feature to distinguish HCC from other malignant lesions. Cholangiocarcinoma may show a similar hypo-enhanced washout during the PVP as HCC, but may be more rapid. ICC may show a peripheral rimlike enhancement during the AP. Metastases may be mostly hypovascular during the AP with a rimlike or diffuse hyperenhancement, and a rapid washout in the PVP and late phase.

Figure 4:
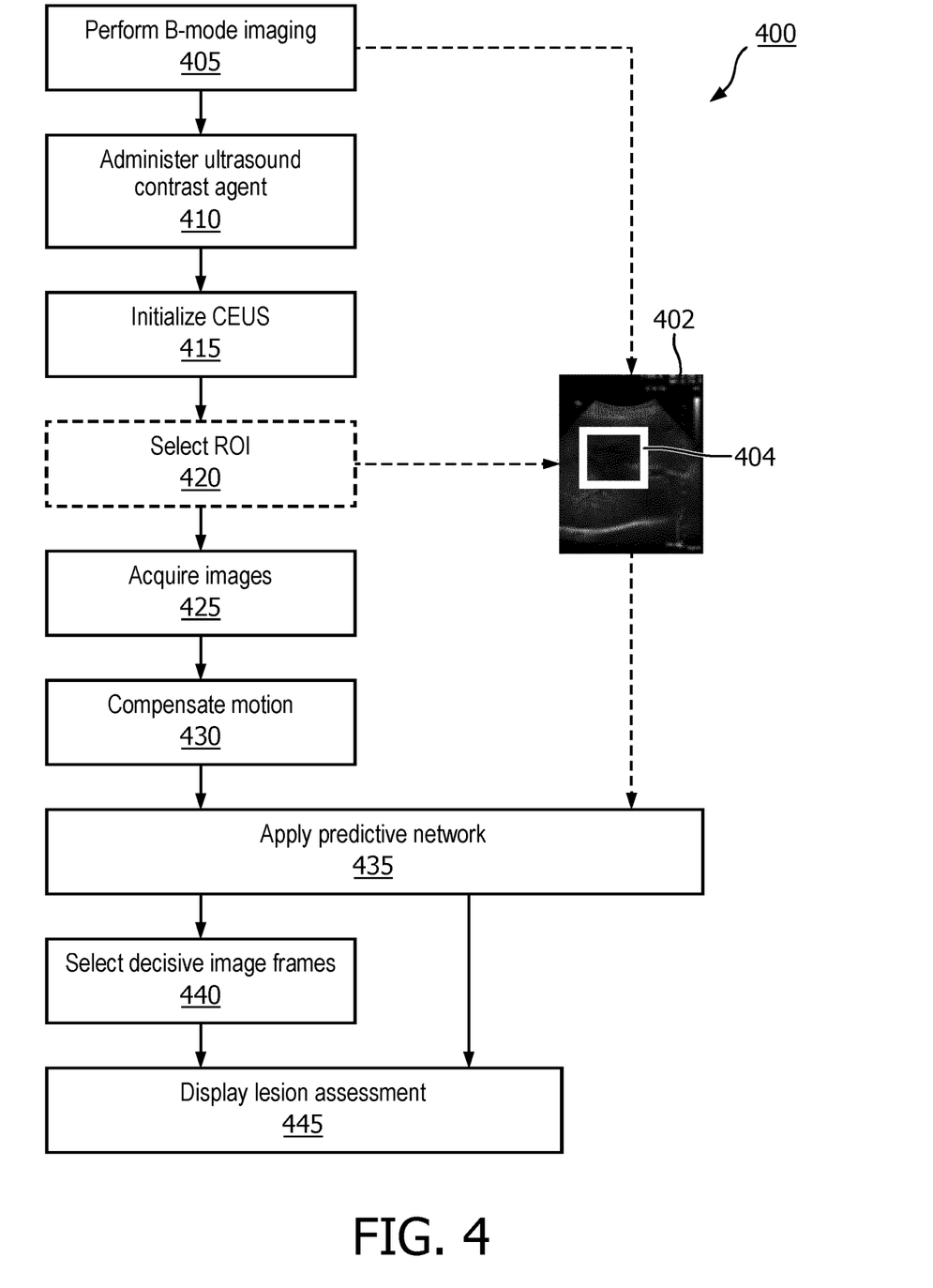
FIG. 4 is a flow diagram illustrating a deep learning-based lesion assessment method, according to aspects of the present disclosure.

FIGS. 4-7 illustrate the use of deep learning-based techniques to automatically and systematically analyze and interpret spatiotemporal variations within CEUS images for assessment of hepatic liver lesions. FIG. 4 is a work flow diagram illustrating a deep learning-based lesion assessment method 400 using CEUS imaging, according to aspects of the present disclosure. The steps of the method 400 can be carried out using the system 100. As illustrated, the method 400 includes a number of enumerated steps, but embodiments of the method 400 may include additional steps before, after, and in between the enumerated steps. In some embodiments, one or more of the enumerated steps may be omitted or performed in a different order. The method 400 will be described below with reference to FIGS. 5, 6, and 7.

At step 405, a clinician may perform B-mode imaging to capture an image 402 of a patient (e.g., the object 105) under a liver lesion assessment using the system 100. The B-mode image 402 may include at least a portion of the patient's liver, hepatic artery, and portal vein. The B-mode image 402 may be displayed on the display 132.

At step 410, the clinician may administer an ultrasound contrast agent to the patient. For example, the clinician may inject a bolus of microbubbles (e.g., of about 1 ml to about 5 ml) into the patient's body.

At step 415, the clinician may initialize the system 100 for CEUS imaging. During initialization, the system 100 may determine or optimize a transmission power, a transmission focal depth, a dynamic range, a signal gain, and/or a transmission frequency for the transducer array 112.

At step 420, the clinician may optionally select a region of interest (ROI) 404 from the B-mode image 402 for the assessment, for example, via an interactive interface on the display 132 or a user input device of the system 100. Alternatively, the processing component 134 may be configured to automatically detect an ROI 404 and display the ROI 404 on the display 132. The selection of the ROI 404 may be used in a later step when applying a deep learning network. The ROI 404 can limit the deep learning network to analyze image portions within the ROI 404. In other words, the ROI 404 can limit the dimension of the input data to the deep learning network, and thus may reduce processing complexity.

At step 425, the system 100 may acquire a sequence of CEUS images of the patient during a period of time after the microbubble injection. For example, the period may include an AP, a PVP, and a late phase as described above. The CEUS images may be stored in the memory 138.

At step 430, the processing component 134 may apply a motion compensation algorithm to the sequence of CEUS images to compensate motions that may arise as the patient breathes in and breathes out. The motion compensation may align the anatomical features in the CEUS images to improve the accuracy of subsequent analysis.

At step 435, the processing component 134 may apply a deep learning network to the motion compensated CEUS images for lesion assessment. For example, the deep learning network can perform spatiotemporal analysis across the CEUS images. The spatiotemporal analysis may combine information of each pixel in the enhancement patterns within the CEUS images with temporal dynamics of the microbubbles (e.g., filling/washout). To reduce the computational complexity and/or time for the processing of the deep learning network, the ROI 404 information can be transferred to the predictive network to limit the spatiotemporal analysis to be within the ROI 404. The architecture of the deep learning network is described in FIG. 5.

Figure 5:
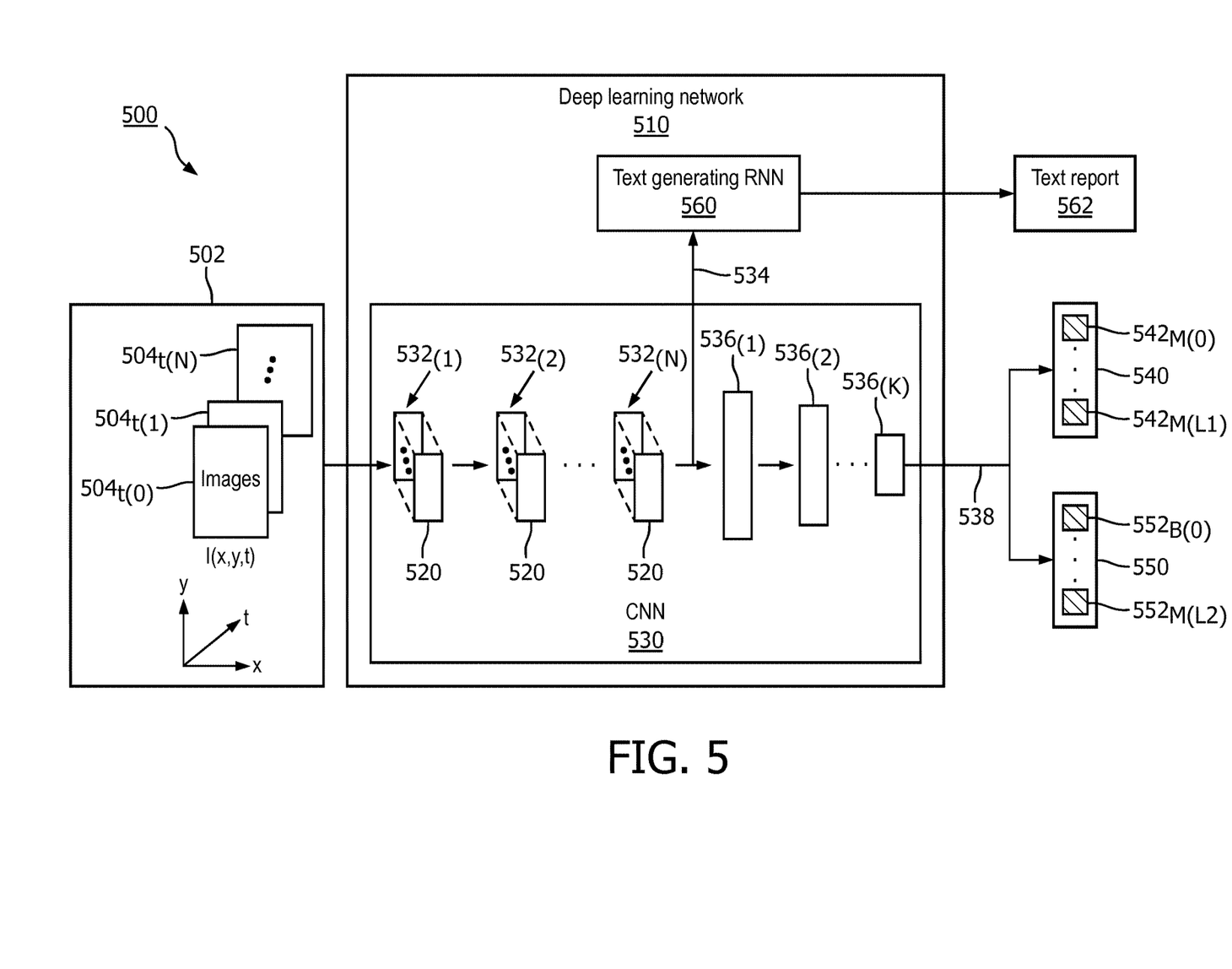
FIG. 5 is a schematic diagram illustrating a configuration of a deep learning network for lesion assessment, according to aspects of the present disclosure.

FIG. 5 is a schematic diagram illustrating a configuration 500 of a deep learning network 510, according to aspects of the present disclosure. The deep learning network 510 can be employed by the method 400 for lesion assessment. The deep learning network 510 may include a CNN 530 and a text generating recurrent neural network (RNN) 560.

The CNN 530 is a three-dimensional (3D) network. The CNN 530 may operate on a sequence 502 of CEUS images 504 across a time period. For example, the CEUS images 504 may correspond to the motion compensated images produced at the step 430 of the method 400. The CNN 530 may include a set of N convolutional layers 532 followed by a set of K fully connected layers 536, where N and K may be any positive integers. The values N and K may vary depending on the embodiments. In some instances, the values N and K may be dependent on the size of the training and/or validation data sets (e.g., the image data set 140). Each convolutional layer 532 may include a set of filters 520 configured to extract features from input images. The features may include spatiotemporal correlations among neighboring pixels (e.g., representative of the microbubbles signatures). Spatiotemporal correlation may refer to the correlation in time and in space among a group or a cluster of neighboring pixels in the images 504. The fully connected layers 536 may be non-linear and may gradually shrink the high-dimensional output of the last convolutional layer $532_{(N)}$ to a length corresponding to the number of classifications at an output 538.

The classifications at the output 538 may include a binary classification between a malignant lesion class 540 and benign lesion class 550. The malignant lesion class 540 may further classify a malignant lesion into L1 plurality of malignant lesion sub-classes 542 (e.g., shown as $542_{M(0)}$ to $542_{M(L1)}$, where L1 is a positive integer). The benign lesion class 550 may further classify a benign lesion into L2 plurality of benign lesion sub-classes 552 (e.g., shown as $552_{B(0)}$ to $552_{B(L2)}$, where L2 is a positive integer). In an embodiment, the malignant lesion subclasses 542 may include HCC, ICC, metastasis and the benign lesion subclasses 552 may include haemangioma, FNH, and Hepatocellular adenoma. In other words, the probability distribution output 538 may indicate a likelihood of a patient having a malignant lesion or a benign lesion and a likelihood of the patient having a particular type of malignant lesion or a particular type of benign lesion.

While not shown in FIG. 5, in some embodiments, the convolutional layers 532 may be interleaved with pooling layers, each including a set of downsampling operations that may reduce the dimensionality of the extracted imaging features. In addition, the convolutional layers 512 may include non-linearity functions (e.g., including rectified non-linear (ReLU) operations) configured to extract rectified feature maps.

The images 504 are shown as $504_{t(1)}$ to $504_{t(N)}$, where $t(1)$ to $t(N)$ may correspond to a time period including an AP, a PVP, and a late phase after a microbubble injection. The images 504 are 2D images (e.g., in an x-y dimensions) across a time period t. The images 504 may be timestamped. Thus, the images 504 can be represented by I(x,y,t). The images 504 may be passed through each layer 532 and 536 in succession for feature extraction, analysis, and/or classification. Each layer 532 or 536 may include weightings (e.g., filter coefficients for the filters 520 in the convolutional layers 532 and non-linear weightings for the fully-connected layers 536) that are applied to the input images 504 or an output of a previous layer 532 or 536.

In an embodiment, the images 504 may be separated into to three subsequences corresponding to the AP, the PVP, and the late phase. For example, the images $504_{t(N0)}$ to $504_{t(N1)}$ may be captured within the AP, the images $504_{t(N1+1)}$ to $504_{t(N2)}$ may be captured within the PVP, and the images $504_{t(N2+1)}$ to $504_{t(N3)}$ may be captured within the late phase, where $1 \leq N0 < N1 < N2 < N3 \leq N$. The CNN 530 may be applied to each subsequence to analyze how the blood flow dynamics and enhancement patterns behave in space and in time during each of the AP, the PVP, and the late phase and across the AP, PVP, and late phase. The CNN 530 may determine a probability distribution for the malignant lesion subclasses 542 and the benign lesion subclasses 552 based on the analysis.

During training, the CNN 530 can be applied to the images in the trained data set 140, for example, using forward propagation, to obtain an output or a score for the images for each malignant lesion subclass 542 and each benign lesion subclass 552. The coefficients of the filters 520 in the convolutional layers 532 and weightings in the fully connected layers 536 can be adjusted, for example, by using backward propagation to minimize the output error. For example, images including HCC can be used to train the CNN 530 such that the CNN 530 may output a high probability (e.g., greater than about 90%) for the subclass 542 corresponding to HCC. In an embodiment, the CNN 530 may be applied to images corresponding to an AP, a PVP, and a late phase to learn how the blood flow dynamics and enhancement patterns behaves in space and time during the AP, the PVP, and the late phase.

The output 534 (e.g., feature maps or feature vectors) at the last convolutional layer $532_{(N)}$ can be input into the text generating RNN 560. The text generating RNN 560 is a learning-based predictive network. Text generation may be achieved with the use of a deep reinforcement learning framework that assimilates clinical diagnosis from clinical reports to produce free-text. For instance, when the ground truth is available, clinical diagnosis can be learnt and the deep learning model may generate a text report with the candidate diagnosis and meaningful features associated with the output 534.

For example, the text generating RNN 560 may include a series of classifiers and/or long short-term memory units (LSTMs). The text generating RNN 560 is trained to generate a text report 562 based on the feature maps (e.g., the output 534). The text generating RNN 560 may extract high-level diagnostic information from the feature map output 534. The text generating RNN 560 may construct the text report 562 based on semantic understanding of the images 504. For example, the text report 562 may provide a description of diagnostic information, highlighting the enhancement patterns during the AP, PVP, and late phase scanning, along with temporal descriptions of the microbubble dynamics, as described in greater detail herein. The text report 562 can be displayed on the display 132. The text report 562 can assist and support user's interpretation of the classifications output (e.g., the probability distribution of the malignant lesion subclasses 542 and the benign lesion subclasses 552) of the CNN 530.

In an embodiment, the coarse binary classification between the malignant lesion class 540 and the benign lesion class 550 may be based on the timing of filling and washout. The CNN 530 may perform the refined classification into the malignant lesion subclasses 542 and the benign lesion subclasses 552 based on the spatiotemporal correlation between microbubbles retrieved in a cluster of neighboring pixels (e.g., the clusters 632 shown in FIG. 6) in the images 504.

Figure 6:
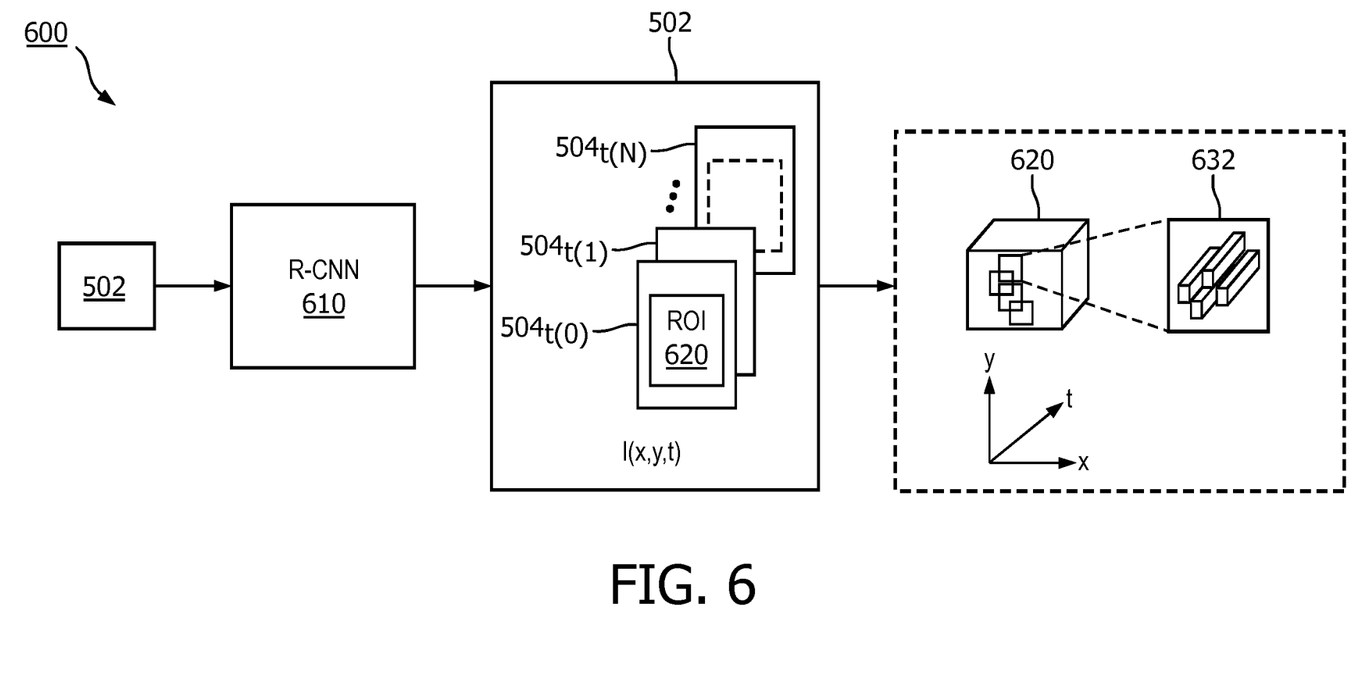
FIG. 6 is a schematic diagram illustrating a region of interest (ROI) detection scheme for lesion assessment, according to aspects of the present disclosure.

FIG. 6 is a schematic diagram illustrating a ROI detection scheme 600 for lesion assessment, according to aspects of the present disclosure. The scheme 600 can be applied in the ROI selection step 420 of the method 400. In the scheme 600, the image sequence 502 may be input into a recurrent-CNN (R-CNN) 610. The R-CNN 610 may have a substantially similar structure as the CNN 530. The R-CNN 610 may determine an ROI 620 (e.g., the ROI 404) in the images 504 of the sequence 502. The R-CNN 610 may identify clusters 632 of neighboring pixels including microbubbles' signatures across the images 504. The clusters 632 of neighboring pixels representing the microbubbles may be input to the CNN 530. The CNN 530 may identify spatiotemporal signatures (e.g., variations of enhancement patterns across time) from the clusters 632 and output the probability distribution at the output 538. The spatiotemporal signatures may have spatiotemporal dimensionalities that are more complex than what human may identify and/or analyze. For example, a physician or a clinician may currently identify a certain type of malignant lesion or a certain type of benign lesion based on analysis at certain points in time and/or certain points in space. The CNN 530 may perform the spatiotemporal correlation across various points in time and/or space and/or at any suitable time and/or space granularities.

Returning to FIG. 4, at step 440, the processing component 134 may further select a set of decisive image frames from the acquired CEUS images (e.g., the images 504). For example, the processing component 134 may select a subset of images from the acquired CEUS images including spatiotemporal features that are most representative of the probability distribution output 538 as shown in FIG. 7.

Figure 7:
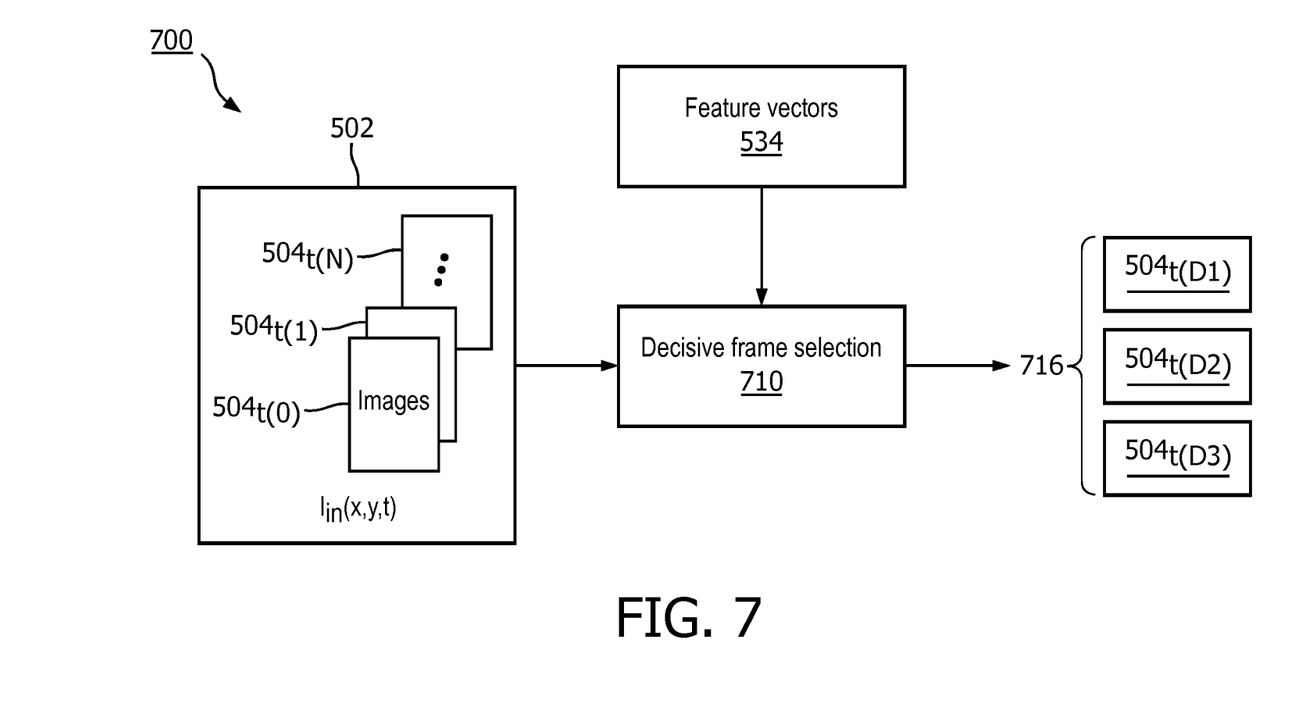
FIG. 7 is a schematic diagram illustrating a decisive frame selection scheme 700 for lesion assessment, according to aspects of the present disclosure.

FIG. 7 is a schematic diagram illustrating a decisive frame selection scheme 700 for lesion assessment, according to aspects of the present disclosure. The scheme 700 can be implemented by the system 100 and may be used in conjunction with the method 400. The scheme 700 includes a decisive frame selection unit 710, which may be implemented by the processing component 134. For example, after applying the CNN 530 to the images 504 to obtain the probability distribution output 538, the decisive frame selection unit 710 may select a subset of the images 504 that are most representative of the probability distribution at the output 538 based on the CNN feature map output 534. In other words, the subset of images 504 and the timestamps associated with the subset may include the most significant features that led the CNN 530 to produce the probability distribution output 538. The subset may be referred to as decisive frames 716. The decisive frame selection unit 710 may output the decisive frames 716. As an example, decisive frame selection unit 710 selects three decisive frames 716 corresponding to the images $504_{t(D1)}$, $504_{t(D2)}$, and $504_{t(D3)}$, where $1 \leq D1, D2, D3 \leq N$. It should be noted that the decisive frame selection unit 710 can select any suitable number of decisive frames (e.g., about 2, 4, 5, or more). The decisive frames 716 can assist a user to understand the outcome of the predictive network (e.g., the deep learning network 510).

The decisive frame selection unit 710 may be implemented using various approaches. For example, the decisive frame selection unit 710 may search the images 504 in the sequence 502 that include spatiotemporal features corresponding to the feature map output 534 of the CNN 530. Alternatively, the decisive frame selection unit 710 may generate a temporal map of correct class probability as a function of importance of the images 504. For example, the temporal map may be a 2D map, denoted as M(x,y,t=frame), where x and y represent the spatial coordinates and t represents time. A local classifier value may be associated with each spatial coordinator ($x_i$, $y_i$). The decisive frame selection unit 710 may determine from the CNN output 534 where in space and in time (which frame) the decision was made. In other words, the decisive frame selection unit 710 may retrieve the spatial features with the highest local probability for each frame from the CNN output 534. The decision may also depend on the different phases (e.g., the AP, PVP, and the late phase). The temporal region in the map with the highest density of the images 504 may determine the decisive frames 716 (e.g., the images $504_{t(D1)}$, $504_{t(D2)}$, and $504_{t(D3)}$).

Figure 8:
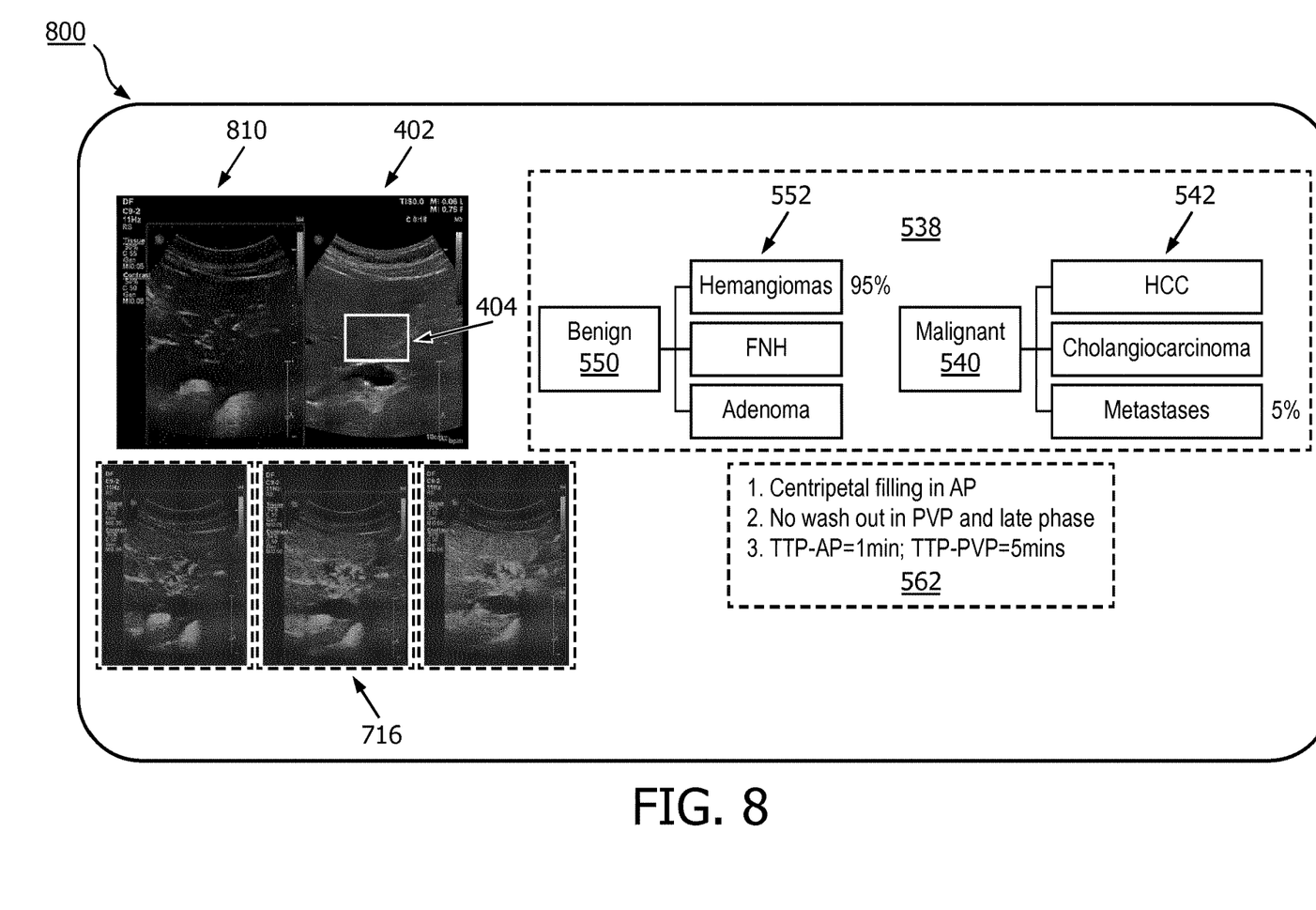
FIG. 8 is a schematic diagram illustrating a display view of a liver lesion assessment, according to aspects of the present disclosure.

Returning to FIG. 4, at step 445, the processing component 134 may send the outputs from the predictive network and the decisive frames for display on the display 132 as shown in FIG. 8.

FIG. 8 is a schematic diagram illustrating an example display view 800 of a liver lesion assessment, according to aspects of the present disclosure. The view 800 may correspond to a display view on the display 132 in the system 100. The view 800 may include the B-mode image 402 including the ROI 404, a CEUS image 810 (e.g., one of the images 504), the probability distribution output 538, the decisive frames 716, and the text report 562.

In the example view 800, the probability distribution output 538 is displayed in tree-structures, for example, a root node for a malignant class (e.g., the malignant lesion class 540) and a root node for a benign class (e.g., the benign lesion class 550). Each root node may branch into different types of malignant lesions (e.g., malignant sub-classes 542) or benign lesions (e.g., benign sub-classes 552). The output 538 indicates a probability of 95 percent (%) for a benign lesion of type Hemangioma and a probability of 5% for a malignant lesion of type metastases. In other words, the patient under the examination is likely to have Hemangioma. In some embodiments, the output 538 may further include a root node for a non-neoplastic lesion class.

The decisive frames 716 show the acquired frames or images that are most representative of the output 538. In other words, the decisive frames 716 can produce about the same probability distribution as the output 538. As an example, the three decisive frames 716 may show probabilities of about 95%, 80%, and 60% for Hemangioma.

The text report 562 may describe the basis of the decision made by the CNN 530. As shown, the text report 562 indicates that a centripetal filing is detected during an AP and that no wash out is detected during a PVP and a late phase. The text report 562 can also indicate a time-to-peak (TTP) value of about 1 minute for the AP and a TTP value of about 5 minutes for the PVP. The TTP value may refer to the amount of time to reach a peak enhancement from the microbubble injection. The centripetal filing during the AP, the no washout during the PVP and the late phase, the TTP of about 1 minute for the AP, and the TTP of about 5 minutes for the PVP and late phase had led the CNN 530 to determine that the lesion is Hemangioma.

Figure 9:
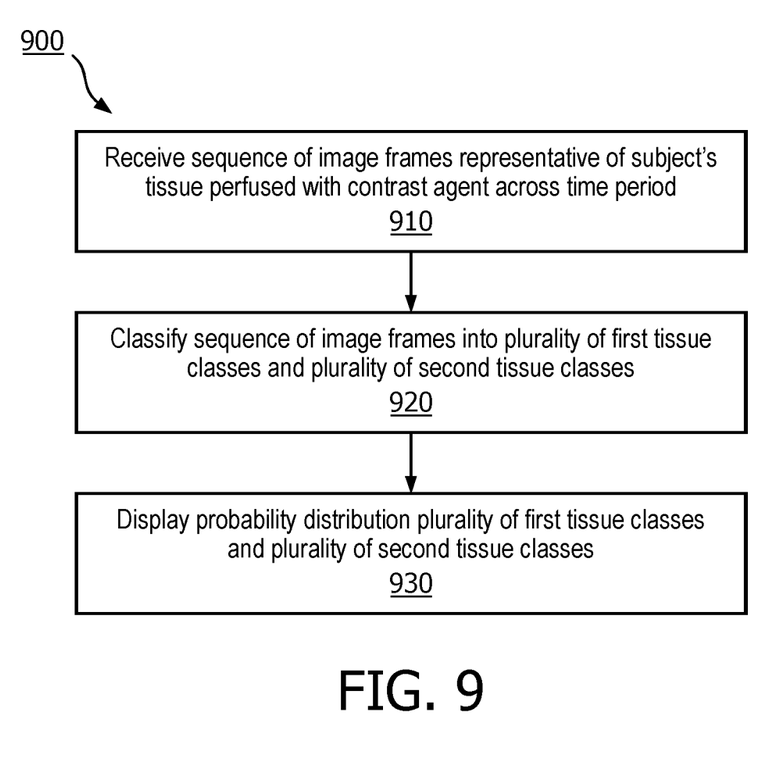
FIG. 9 is a flow diagram of an automated lesion assessment method, according to aspects of the present disclosure.

FIG. 9 is a flow diagram of an automated lesion assessment method 900, according to aspects of the present disclosure. Steps of the method 900 can be executed by a computing device (e.g., a processor, processing circuit, and/or other suitable component) of an ultrasound imaging probe, such as the probe 110, or a host such as the host 130. The method 900 may employ similar mechanisms as in the method 400, the configuration 500, and the schemes 600, and 700 described with respect to FIGS. 4, 5, 6, and 7, respectively. As illustrated, the method 900 includes a number of enumerated steps, but embodiments of the method 900 may include additional steps before, after, and in between the enumerated steps. In some embodiments, one or more of the enumerated steps may be omitted or performed in a different order.

At step 910, the method 900 includes receiving, from an imaging device (e.g., the transducer array 112), a sequence (e.g., the sequence 502) of image frames (e.g., the CEUS images 504) representative of a subject's tissue (e.g., the object 105) perfused with a contrast agent across a time period.

At step 920, the method 900 includes classifying the sequence of image frames into a plurality of first tissue classes (e.g., the malignant lesion class 542) and a plurality of second tissue classes (e.g., the benign lesion sub-classes 552). The classification may be based on a spatiotemporal correlation among the sequence of image frames. The classification may include applying a predictive network to the sequence of image frames to produce a probability distribution (e.g., the output 538) for the plurality of first tissue classes and the plurality of second tissue classes. For example, the predictive network may include a CNN similar to the CNN 530 that performs the classification.

At step 930, the method 900 includes displaying, by a display (e.g., the display 132), the probability distribution for the plurality of first tissue classes and the plurality of second tissue classes.

In an embodiment, the display may display a probability for each of the plurality of first tissue classes a probability for each of the plurality of second tissue classes, for example, in a tree-structure as shown in the view 800.

In an embodiment, the method 900 may include identifying, by the predictive network, a subset of the sequence of image frames (e.g., the decisive frames 716) that are most representative of the probability distribution. The method 900 may include displaying, by the display, an image frame in the subset.

In an embodiment, the method 900 may include generating, by the predictive network, a text report (e.g., the text report 562) including information associated with perfusion of the contrast agent through the subject's tissue during different sub-periods (e.g., an AP, a PVP, and/or a late phase) of the time period based on the spatiotemporal correlation. The method 900 may include displaying, by the display, the text report. For example, the predictive network may include an RNN similar to the RNN 560 that generates the text report.

In an embodiment, the method 900 may include identifying an ROI (e.g., the ROI 404) from the subject's tissue based on the sequence of image frames. The method 900 may include applying the predictive network based on the identified ROI. For example, the predictive network may include an R-CNN similar to the R-CNN 610 that identifies the ROI.

In an embodiment, the subject's tissue may include at least a portion of a liver. The plurality of first tissue classes may include at least one of hepatocellular carcinoma (HCC), cholangiocarcinoma, or metastasis. The plurality of second tissue classes may include at least one of hemangioma, focal nodular hyperplasia (FNH), or adenoma In an embodiment, the predictive network may be trained by providing a sequence of test image frames representative of a contrast agent perfused test subject's tissue across a time period. The training may include sorting the sequence of test image frames based on an AP of perfusion of the contrast agent through the test subject's tissue, a PVP of the perfusion, and a late phase of the perfusion. The training may include assigning scores to the sequence of test image frames based on spatiotemporal characteristics of blood flow associated with the plurality of first tissue classes and the plurality of second tissue classes.

Aspects of the present disclosure can provide several benefits. For example, the use of deep learning networks can automate lesion assessments (classification and characterization), providing assistances to guide clinicians in differentiating between different types of malignant and benign lesions. In addition, the automating can provide more consistent lesion assessment results, eliminating variations that can arise from different interpretations across different clinicians, and allowing for diagnosis by non-expert users. Further, the deep learning network may learn and identify spatiotemporal signatures in spatiotemporal dimensionalities that are more complex than what human may identify and/or analyze. The displaying of the classification output (e.g., the probability distribution) along with the text report and decisive frames can further guide and support a user in interpretation of CEUS images for lesion assessment. The disclosed embodiments may also be used in conjunction with current clinical practices and scanning protocols in lesion assessment to increase the confidence level of a diagnosis or assessment by a clinician. Thus, the disclosed embodiments can also add values to current clinical practices in lesion assessment. While the disclosed embodiments are described in the context of applying deep learning based techniques to classify tissues from CEUS images, the disclosed embodiments can be applied to classify tissues from images of other modes such as MRI, CT, and/or X-ray. For example, the images 504 can be MRI images, CT images, or X-ray images.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A clinical assessment system, comprising:
a processor in communication with an imaging device, wherein the processor is configured to:
receive, from the imaging device, a sequence of image frames representative of a subject's tissue perfused with a contrast agent across a time period;
classify the sequence of image frames into a plurality of first tissue classes and a plurality of second tissue classes different from the first tissue classes, the classification based on a spatiotemporal correlation among the sequence of image frames by applying a predictive network to the sequence of image frames to produce a probability distribution for the plurality of first tissue classes and the plurality of second tissue classes wherein the predictive network identifies a subset of the sequence of image frames that are most representative of the probability distribution; and
output, to a display in communication with the processor, the probability distribution for the plurality of first tissue classes and the plurality of second tissue classes and an image frame in the subset.

2. The system of claim 1, wherein the processor is further configured to:
output, to the display, a probability for each of the plurality of first tissue classes; and
output, to the display, a probability for each of the plurality of second tissue classes.

3. The system of claim 1, wherein the spatiotemporal correlation is among pixels in the sequence of image frames representing perfusion of the contrast agent through the subject's tissue.

4. The system of claim 3, wherein the predictive network produces a text report including information associated with the perfusion of the contrast agent through the subject's tissue during different sub-periods within the time period based on the spatiotemporal correlation, and wherein the processor is further configured to:
output, to the display, the text report.

5. The system of claim 4, wherein the predictive network includes a first predictive sub-network and a second predictive sub-network, wherein the first predictive sub-network produces the probability distribution, and wherein the second predictive sub-network produces the text report.

6. The system of claim 4, wherein the sub-periods include at least one of an arterial phase (AP) of the perfusion, a portal venous phase (PVP) of the perfusion, or a late phase of the perfusion.

7. The system of claim 1, wherein the subject's tissue includes at least a portion of a liver.

8. The system of claim 7, wherein the plurality of first tissue classes includes at least one of hepatocellular carcinomas (HCC), cholangiocarcinoma, or metastasis, and wherein the plurality of second tissue classes includes at least one of hemangioma, focal nodular hyperplasia (FNH), or adenoma.

9. The system of claim 1, wherein the processor is configured to:
output, to the display, a brightness-mode (B-mode) image representative of the subject's tissue.

10. The system of claim 1, wherein the processor is configured to:
output, to the display, a contrast-enhanced image of the subject's tissue based on the sequence of image frames.

11. The system of claim 1, wherein the processor is further configured to:
receive, from a user input device in communication with the processor, an indication of a selected region of interest (ROI) of the subject's tissue; and
apply the predictive network to the sequence of image frames based on the selected ROI.

12. The system of claim 1, wherein the processor is configured to:
identify a region of interest (ROI) from the subject's tissue based on the sequence of image frames; and
apply the predictive network to the sequence of image frames based on the identified ROI.

13. The system of claim 1, wherein the predictive network is trained by:
providing a sequence of test image frames representative of a contrast agent perfused test subject's tissue across a time period;
sorting the sequence of test image frames based on an arterial phase (AP) of perfusion of the contrast agent through the test subject's tissue, a portal venous phase (PVP) of the perfusion, and a late phase of the perfusion; and
assigning scores to the sequence of test image frames based on spatiotemporal characteristics of blood flow associated with the plurality of first tissue classes and the plurality of second tissue classes.

14. A method of clinical assessment, comprising:
receiving, from an imaging device, a sequence of image frames representative of a subject's tissue perfused with a contrast agent across a time period;
classifying the sequence of image frames into a plurality of first tissue classes and a plurality of second tissue classes different from the first tissue classes, the classification based on a spatiotemporal correlation among the sequence of image frames by applying a predictive network to the sequence of image frames to produce a probability distribution for the plurality of first tissue classes and the plurality of second tissue classes;
identifying, by the predictive network, a subset of the sequence of image frames that are most representative of the probability distribution; and
displaying, by a display, the probability distribution for the plurality of first tissue classes and the plurality of second tissue classes and an image frame in the subset.

15. The method of claim 14, wherein the displaying includes:
displaying a probability for each of the plurality of first tissue classes; and
displaying a probability for each of the plurality of second tissue classes.

16. The method of claim 14, further comprising:
generating, by the predictive network, a text report including information associated with perfusion of the contrast agent through the subject's tissue during different sub-periods of the time period based on the spatiotemporal correlation; and
displaying, by the display, the text report.

17. The method of claim 14, further comprising:
identifying a region of interest (ROI) from the subject's tissue based on the sequence of image frames; and
applying the predictive network based on the identified ROI.

18. The method of claim 14, wherein the subject's tissue includes at least a portion of a liver, wherein the plurality of first tissue classes includes at least one of hepatocellular carcinoma (HCC), cholangiocarcinoma, or metastasis, and wherein the plurality of second tissue classes includes at least one of hemangioma, focal nodular hyperplasia (FNH), or adenoma.

* * * * *